(12) United States Patent
Wright et al.

(10) Patent No.: US 6,677,370 B2
(45) Date of Patent: Jan. 13, 2004

(54) COMPOSITIONS AND USES OF DICTYOSTATIN COMPOUNDS

(75) Inventors: Amy E. Wright, Ft. Pierce, FL (US); Jennifer L. Cummins, Hackettstown, NJ (US); Shirley A. Pomponi, Ft. Pierce, FL (US); Ross E. Longley, Vero Beach, FL (US); Richard A. Isbrucker, Toronto (CA)

(73) Assignee: Harbor Branch Oceanographic Institution, Inc., Fort Pierce, FL (US)

( * ) Notice: Subject to any disclaimer, the term of this patent is extended or adjusted under 35 U.S.C. 154(b) by 0 days.

(21) Appl. No.: 10/360,200

(22) Filed: Feb. 6, 2003

(65) Prior Publication Data

US 2003/0153615 A1 Aug. 14, 2003

Related U.S. Application Data

(62) Division of application No. 09/793,323, filed on Feb. 26, 2001.
(60) Provisional application No. 60/184,617, filed on Feb. 24, 2000.

(51) Int. Cl.$^7$ ............................................. A61K 31/335
(52) U.S. Cl. ....................................................... 514/450
(58) Field of Search ......................................... 514/450

(56) References Cited

U.S. PATENT DOCUMENTS

| | | | |
|---|---|---|---|
| 4,206,221 A | 6/1980 | Miller et al. | |
| 4,960,790 A | 10/1990 | Stella et al. | |
| 5,157,049 A | 10/1992 | Haugwitz et al. | |
| 5,430,053 A | 7/1995 | Pettit et al. | |

OTHER PUBLICATIONS

Barrand et al. "Multidrug Resistance–Associated Protein: A Protein from P–glycoprotein Involved in Cytotoxic Drug Expulsion"*Gen. Pharmac.,* 1997, pp 639–345, vol. 28, No. 5, Elsevier Science Inc., USA.
Bellamy, B.T. "P–Glycoproteins And Multidrug Resistance" *Annu. Rev. Pharmacol. Toxicol.,* 1996, pp 161–183, vol. 36, Annual Reviews Inc.
Broxterman, H.J. et al. "Multidrug Resistance Proteins and Other Drug Transport–Related Resistance to Natural Product Agents" *Current Opinion in Oncology,* 1995, pp 532–540, Vol 7, Rapid Science Publishers.
Bollag, D.M. et al. "Epothilones, A New Class of Microtubule–Stabilizing Agents With A Taxol–Like Mechanism of Action" *Cancer Research,* Jun. 1, 1995, pp 2325–2333, American Association for Cancer Research, Inc., USA.
Casazza A.M. and Fairchild C.R. "6. Paclitaxel (Taxol®) Mechanisms of Resistance" *Resistance to Microtubule Active Drugs,* pp 149–171. (1996).
D'Ambrosio, M. et al. "On the Novel Free Porphyrins Corallistin B, C, D, and E: Isolation from the Demosponge Corallistes sp. Of the Coral Sea and Reactivity of Their Nickel (II) Complexes Toward Formylating Reagents" *Helv. Chim. Acta,* 1993, pp 1489–1496, vol. 76 No. 4.
Dustin P. "Microtubules: They Are Structural Organelles That Are Found In All Nucleated Cells. Assembled Like Scaffolding From Protein Subunits, They Participate In Cell Division, Cell Movement And The Maintenance Of Cell Shape" *Scientific American,* Aug. 1980, pp 67–76, vol. 243. No 2, Scientific American, Inc.
Fuchs D.A. and Johnson R.K. "Cytologic Evidence That Taxol, an Antineoplastic Agent From *Taxus Brevifolia,* Acts as a Mitotic Spindle" *Cancer Treatment Reports,* Aug. 1978, pp 1219–1222, vol. 62 No. 8.
Gunasekera S.P. et al. "Discodermolide: A New Bioactive Polyhydroxylated Lactone From The Marine Sponge *Discodermia dissoluta" J. Org. Chem.,* 1990, pp 4912–4915, vol. 55, American Chemical Society.
Komarov et al. "Activation of the LRP (Lung Resistance–Related Protein) Gene by Short–Term Exposure of Human Leukemia Cells to Phorbel Ester and Cytarbine" *Oncology Research,* 1998, pp 185–192, vol. 10, Cognizant Comm. Corp., USA.
Kowalski R.J. et al. "The Microtubule–Stabilizing Agent Discodermolide Competitvely Inhibits the Binding of Paclitaxel (Taxol) to Tubulin Polymers, Enhances Tubulin Nucleation Reactions More Potently than Paclitaxel, and Inhibis the Growth of Paclitaxel–Resistance Cells" *Molecular Pharmacology,* 1997, pp 613–622, vol. 52, The American Society for Pharmacology and Experimental Therapuetics.
Krishan, A. et al. "Drug Retention, Efflux, and Resistance in Tumor Cells" *Cytometry,* 1997, pp 279–285, vol. 29, Wiley–Liss. Inc.
Kruh, G.D. et al. "Expression Pattern of MRP in Human Tissues and Adult Solid Tumor Cell Lines" *Journal of the National Cancer Institute,* Aug. 16, 1995, vol. 87, No. 16.
Lindel, T. et al. "Eleutherobin, A New Cytotoxin that Mimics Paclitaxel (Taxol) by Stabilizing Microtubules" *J. Am. Chem. Soc.,* 1997, pp 8744–8745, vol. 119., American Chemical Society.
Longley, R.E. et al. "Immunosuppression by Discodermolide" *Annals New York Of Science,* 1993 pp 94–107, New York Academy of Science.
Miller D.W. et al. "The Expression of Multidrug Resistance–Associated Protein (MRP) in Pancreatic Adenocarcinoma Cell Lines" *Cancer Letters,* 1996, pp 301–306, vol. 107, Elsevier Science Ireland Ltd.

(List continued on next page.)

*Primary Examiner*—Jerome D. Goldberg
(74) *Attorney, Agent, or Firm*—Saliwanchik, Lloyd & Saliwanchik

(57) ABSTRACT

Dictyostatin-1 has been found to stabilize microtubules and prohibit their depolymerization to free tubulin. Because of these activities, the dictyostatin compounds can be used in the treatment of a number of diseases in which aberrant cellular proliferation occurs such as drug-sensitive and drug-resistant cancers, autoimmune disorders, and inflammatory diseases.

6 Claims, 7 Drawing Sheets

(3 of 7 Drawing Sheet(s) Filed in Color)-

OTHER PUBLICATIONS

Mooberry, S. . et al. "Laulimalide and Isolaulimide, New Oaclitaxel–Like Microtubule–Stabilizing Agents" *Cancer Research,* Feb. 1, 1999, pp. 653–660, vol. 59.

Pettit, G.R. et al. "Isolation and Structure of the Cancer Cell Growth Inhibitor Dicytostatin 1" *J. Chem. Soc., Chem. Commun* 1994, pp 1111–1112, The Royal Society of Chemistry.

Rein, T. "Asymmetric Horner–Wadsworth–Emmons Reactions With Aldehyde Substrates: Scope and Synthetic Applications" *Book of Abstracts, 213th ACS National Meeting,* San Francisco, Apr. 13–17, 1997, Orgn–400 Publisher: American Society, Washington D.C.

Rowinski, E.K. and Donehower, R.C. "Review ArPaclitaxel (Taxol)" *The New England Journal of Medicine,* Apr. 13, 1995, pp 1004–1014, vol. 332 No. 15.

Schiff, P.B. et al. "Promotion of Microtubule Assembly in vitro by Taxol" *Nature,* Feb. 22, 1979, pp. 665–667, Macmillan Journals Ltd.

Ter Harr, H. et al. "Discodermolide, A Cytotoxic Marine Agent That Stabilizes Microtubules More Potently Than Taxol" *Biochemistry,* 1996, pp. 243–250, Vol: 35, American Chemical Society.

Wilson, L. "Microtubule as Drug Receptors: Pharmacological Properties of Microtubule Protein" *Part III: The Pharmacology of Antimitotic Drugs,* 1975, pp 213–231, vol. 253, The New York Academy of Sciences.

COMPOSITIONS AND USES OF DICTYOSTATIN COMPOUNDS

CROSS-REFERENCE TO A RELATED APPLICATION

This application is a divisional of co-pending application U.S. Ser. No. 09/793,323, filed Feb. 26, 2001. This application also claims the benefit of U.S. Provisional Application No. 60/184,617, filed Feb. 24, 2000.

BACKGROUND OF THE INVENTION

Of great importance to man is the control of pathological cellular proliferation. While certain methods and chemical compositions have been developed which aid in inhibiting, remitting, or controlling cellular proliferation, new methods and compositions are needed.

In searching for new biologically active compounds, it has been found that some natural products and organisms are potential sources for chemical molecules having useful biological activity of great diversity. For example, the diterpene commonly known as taxol, isolated from several species of yew trees, is a mitotic spindle poison that stabilizes microtubules and inhibits their depolymerization to free tubulin (Fuchs, D. A., R. K. Johnson (1978) *Cancer Treat. Rep.* 62:1219–1222; Schiff, P. B., J. Fant, S. B. Horwitz (1979) *Nature* (London) 22:665–667). Taxol is also known to have antitumor activity and has undergone a number of clinical trials which have shown it to be effective in the treatment of a wide range of cancers (Rowinski, E. K., R. C. Donehower (1995) *N. Engl. J. Med.* 332:1004–1014). See also, e.g., U.S. Pat. Nos. 5,157,049; 4,960,790; and 4,206,221.

Marine sponges have also proven to be a source of biologically active chemical molecules. A number of publications disclose organic compounds derived from marine sponges including Scheuer, P. J. (ed.) *Marine Natural Products, Chemical and Biological Perspectives*, Academic Press, New York, 1978–1983, Vol. I–V; Uemura, D., K. Takahashi, T. Yamamoto, C. Katayama, J. Tanaka, Y. Okumura, Y. Hirata (1985) *J. Am. Chem. Soc.* 107:4796–4798; Minale, L. et al. (1976) *Fortschr. Chem. org. Naturst.* 33:1–72; Faulkner, D. J. (1998) *Natural Products Reports* 15:113–158; Gunasekera, S. P., M. Gunasekera, R. E. Longley and G. K. Schulte (1990) *J. Org. Chem.*, 55:4912–4915.

A prime target for the discovery and design of novel therapeutic agents against cancer is the mitotic apparatus of the cell and more specifically, microtubule assembly and its function (Wilson, L. (1975) "Microtubules as drug receptors: pharmacological properties of microtubule protein" *Ann. N.Y. Acad. Sci.* 253:213–231). Ancillary functions of microtubules, including intracellular transport, signal transduction and the maintenance of cellular shape and motility are important factors which contribute to the overall growth of tumor cells and resulting metastases (Dustin, P. (1980) *Sci. Am.* 243:66–76). Taxol is a microtubule interactive agent whose mechanism of action includes the premature polymerization of tubulin, resulting in hyperstable microtubule formation, blockage of cellular proliferation in the $G_2/M$ phase of the cell cycle, mitotic spindle disorganization and cell death. Additional compounds, which are chemically unrelated to Taxol, are rapidly coming onto the scene which share a similar mechanism of action with Taxol and are the subject of intense research into their potential as novel antitumor agents. These include the epothilones A and B, macrolides isolated from a myxobacterium, *Sorangium cellulosum* (Bollag, D. M., P. A. McQueney, J. Zhu et al. (1995) *Cancer Res.* 55:2325–2333); eleutherobin, obtained from a marine soft coral (Lindel, T., P. R. Jensen, W. Fenical et al. (1997) *J. Am. Chem. Soc.* 119:8744–8745); laulimalide, isolated from a marine sponge (Mooberry, S. L., G. Tien, A. H. Hernandez et al. (1999) *Cancer Res.* 59:653–660); and discodermolide isolated from a marine sponge (Gunasekera, S. P., M. Gunasekera, R. E. Longley (1990) *J. Org. Chem.* 55:4912–4915 and Ter Haar E., R. J. Kowalski, E.Hamel, et. al. (1996) *Biochemistry* 3:243–250). All of these compounds induce microtubule hyperstabilizing activity and are cytotoxic in vitro to tumor cells in the nanomolar range.

The success of chemotherapy for the treatment of various cancers can be substantially negated though cellular mechanisms which have evolved to enable neoplastic cells to subvert the cytotoxic effects of the drug. Some cells have developed mechanisms, which confer resistance to a number of structurally unrelated drugs. This multi-drug resistance (or MDR) phenomenon may arise through a number of different mechanisms. One of these involves the ability of a cell to reduce intracellular concentrations of a given drug through efflux from cytoplasm through and out the cell membrane by a series of unique ATP-dependent transporter proteins called-P-glycoproteins (Pgp) (Casazza, A. M. and C. R. Fairchild (1996) *Cancer Treat Res.* 87:149–171). The surface membrane, 170 kDa Pgp, is encoded by the mdr-1 gene and appears to require substrate binding before transport begins. A wide range of compounds including a number of structurally unrelated chemotherapeutic agents (adriamycin, vinblastine, colchicine, etoposide and Taxol), are capable of being transported by Pgp and render the cell resistant to the cytotoxic effects of these compounds. While many normal cell types possess Pgp, in general, tumor cell lines, which possess high levels of mRNA specific for Pgp, also exhibit overexpression of membrane Pgp and demonstrate resistance to various drugs. This intrinsic resistance can be increased multifold by incubation of cells with stepwise increasing doses of a particular drug over a period of several months. This can be further facilitated by the addition of the MDR reversal agent, verapamil (Casazza, A. M. and C. R. Fairchild (1996) supra) in combination with the particular drug. Drug resistant cell lines produced in this fashion exhibit resistance to drug cytotoxicity from 20 to 500 fold, compared to parental cell lines.

An additional target for cancer drug discovery is a high molecular weight membrane protein associated with multidrug resistance properties of certain tumor cells known as the multidrug resistance-associated protein (MRP). MRP is a 190 kD membrane-bound glycoprotein (Bellamy, W. T. (1996), *Annu. Rev. Pharmacol. Toxicol.*, 36: 161–183) which belongs to the same family of proteins as the p-glycoprotein pump P-gp (Broxterman, H. J., Giaccone, G., and Lankelma, J. (1995), *Current Opinion in Oncology*, 7:532–540) but shares less than 15% homology of amino acids with P-gp (Komorov, P. G., Shtil, A. A., Holian, O., Tee, L., Buckingham, L., Mechetner, E. B., Roninson, I. B., and Coon, J. S. (1998), *Oncology Research*, 10: 185–192). MRP has been found to occur naturally in a number of normal tissues, including liver, adrenal, testis, and peripheral blood mononuclear cells (Krishan, A., Fitz, C. M., and Andritsch, I. (1997), *Cytometry* 29: 279–285). MRP has also been identified in tissues of the lung, kidney, colon, thyroid, urinary bladder, stomach, spleen (Sugawara, I. (1998) *The Cancer Journal* 8(2)) and skeletal muscle (Kruh, G. D., Gaughan, K. T., Godwin, A., and Chan, A. (1995) *Journal of the National Cancer Institute* 87(16): 1256–1258). High levels of MRP have been implicated in multidrug resistance (MDR) in cancers of the lung and pancreas (Miller, D. W., Fontain, M., Kolar, C., and Lawson, T. (1996) *Cancer Letters* 107: 301–306), and in neuroblastomas, leukemias and cancer of the thyroid (Kruh, G. D., Gaughan, K. T., Godwin, A., and Chan, A. (1995) *Journal of the National Cancer Institute* 87(16): 1256–1258), as well as bladder, ovarian and breast cancers (Barrand, M., Bagrij, T., and Neo, S. (1997) *General Pharmacology* 28(5): 639–645). MRP-mediated MDR involves some of the same classes of compounds as those which are mediated by P-gp, including vinca alkaloids, epipodophyllotoxins, anthracyclins and actinomycin D (Barrand, M., Bagrij, T., and Neo, S. (1997) *General Pharmacology* 28(5): 639–645). However, the substrate specificity has been demonstrated to differ from that of P-gp (Komorov, P. G., Shtil, A. A., Holian, O., Tee, L., Buckingham, L., Mechetner, E. B., Roninson, I. B., and Coon, J. S. (1998) *Oncology Research* 10: 185–192). Drugs which would inhibit or which are not substrates for the MDR pump would, therefore, be useful as chemotherapeutic agents.

Some cancer cell lines, which have been induced to develop resistance to one type of microtubule interactive agent such as Taxol, have been found to be sensitive to other types of microtubule agents. For example, the chemically unrelated compounds epothilones (A and B), which are isolated from a myxobacterium, *Sorangium cellulosum* and are composed of 16 membered macrolides (Bollag, D. M., P. A. McQueney, J. Zhu et al. (1995) *Cancer Res.* 55:2325–2333) enhance microtubule stability, block cells in the $G_2/M$ phase of the cell cycle and prevent microtubule depolymerization in cancer cells, similar to Taxol. The epothilones also have a much greater cytotoxicity against p-glycoprotein expressing, multidrug resistant cells compared to non-multi-drug resistant cell lines.

Laulimalide and isolaulimalide, are two compounds which share Taxol's microtubule-stabilizing activity (Mooberry, S. L., G. Tien, A. H. Hernandez et al. (1999) *Cancer Res.* 59:653–660), but are not chemically related to Taxol. Laulimalide is a potent inhibitor of cellular proliferation with $IC_{50}$ values in the low nanomolar range, whereas isolaulimalide is much less potent with $IC_{50}$ values in the low micromolar range. Both compounds inhibit cellular replication at the $G_2/M$ phase of the cell cycle. Laulimalide and isolaulimalide inhibit the proliferation of SKVLB-1 cells, a Pgp overexpressing multidrug-resistant cell line, again, suggesting that they are poor substrates for transport by Pgp.

Discodermolide, a compound derived from the marine sponge, Discodermia dissoluta (Gunasekera, S. P., M. Gunasekera, R. E. Longley (1990) *J. Org. Chem.* 55:4912–4915), is a potent inhibitor of cellular proliferation and has a similar mechanism of action to Taxol. Discodermolide blocks cells in the $G_2/M$ phase of the cell cycle (Longley, R. E., S. P. Gunasekera, D. Faherty et al. (1993) Immunosuppression by discodermolide. In: A. C. Allison ed. Annals of the New York Academy of Sciences Conference Proceedings, "Immunosuppressive and Anti-inflammatory Drugs" Vol. 696, April 12–15) and induces the hyperstabilization of microtubules in cells, leading to cell death (ter Harr, E., Kowalski et al. (1996) *Biochemistry* 35:243–250). Discodermolide also inhibits the proliferation of Pgp overexpressing, multidrug-resistant cell lines (Kowalski, R. J. et al. (1997) *Mol. Pharmacol.* 52:613–622).

The prevention and control of inflammation is also of great importance for the treatment of humans and animals. Much research has been devoted to development of compounds having anti-inflammatory properties. Certain methods and chemical compositions have been developed which aid in inhibiting or controlling inflammation, but additional anti-inflammatory methods and compositions are needed.

Immunomodulation is a developing segment of immunopharmacology. Immunomodulator compounds and compositions, as the name implies, are useful for modulating or regulating immunological functions in animals. Immunomodulators may be immunostimulants for building up immunities to, or initiate healing from, certain diseases and disorders. Conversely, immunomodulators may be immunoinhibitors or immunosuppressors for preventing undesirable immune reactions of the body to foreign materials, or to prevent or ameliorate autoimmune reactions or diseases.

Immunomodulators have been found to be useful for treating systemic autoimmune diseases, such as lupus erythematosus and diabetes, as well as immunodeficiency diseases. Further, immunomodulators may be useful for immunotherapy of cancer or to prevent rejections of foreign organs or other tissues in transplants, e.g., kidney, heart, or bone marrow.

Various immunomodulator compounds have been discovered, including FK506, muramylic acid dipeptide derivatives, levamisole, niridazole, oxysuran, flagyl, and others from the groups of interferons, interleukins, leukotrienes, corticosteroids, and cyclosporins. Many of these compounds have been found, however, to have undesirable side effects and/or high toxicity. New immunomodulator compounds are therefore needed to provide a wider range of immunomodulator function.

Dictyostatin-1 is a macrolide of polyketide origin which was first reported by Pettit et al. from a sponge of the genus Spongia collected in the Republic of the Maldives. (G. R. Pettit, Z. A. Cichacz, F. Gao, M. R. Boyd and J. M. Schmidt, (1994), "Isolation and Structure of the cancer Cell Growth hibitor Dictyostatin-1" *J. Chem. Soc. Chem. Comm.* 1111–1112) U.S. Pat. No. 5,430,053 (incorporated herein in its entirety by reference) describes the isolation and structure of dictyostatin-1 as well as its ability to inhibit the growth of various cancer cell lines in vitro. These reports do not disclose any utility for the compound against multi-drug resistant tumors in animals or humans or the ability of dictyostatin-1 to induce microtubule hyperstabilizing activity.

BRIEF SUMMARY OF THE INVENTION

The subject invention provides novel uses for the dictyostatin class of compounds. These new uses include the control of cellular proliferation, cytotoxicity against human tumor cells resistant to chemotherapeutic agents, immunomodulation, and the control of inflammation. These uses arise from the identification of the role of dictyostatin compounds as tubulin polymerizers and microtubule stabilizers.

In accordance with the subject invention it has been determined that, when tubulin is treated with dictyostatin-1, a rapid onset of polymerization occurs in the absence of cells. This effect is not reversed upon temperature change indicating a long term stabilization of the microtubules. Also, PANC-1 human pancreatic adenoma cells treated with dictyostatin-1 do not undergo mitosis and show pronounced rearrangement of the microtubules in the cells.

The identification of dictyostatins as tubulin polymerizers and microtubule stabilizers facilitates the use of these compounds in a variety of clinical settings. The ability of the compound to inhibit the proliferation of human tumor cells which possess resistance to various chemotherapeutic agents is also embodied in this invention. The subject invention, would, therefore, have utility in the treatment of various human cancers which may have developed resistance to certain chemotherapeutic agents. Thus, the compounds of the subject invention are useful in the treatment of multi-drug resistant cancers.

The effects of dictyostatin-1 on tubulin polymerization microtubule stabilization and cytotoxicity towards human tumor cells which possess resistance to various chemotherapeutic agents could not be predicted either from the structure of the dictyostatin compounds or the previously reported data. In view of the unique and advantageous mode of action of the dictyostatin compounds, these compounds can be used in the treatment of a number of conditions in which aberrant cellular proliferation occurs. These conditions include, for example, autoimmune disorders and inflammatory diseases. In addition to use in the treatment of these disorders as well as other conditions involving pathological cellular proliferation, the compounds of the current invention can also be used as biochemical tools to study the process of tubulin polymerization/depolymerization and drug resistance.

In a preferred embodiment, the dictyostatin-1 compound of the subject invention has the following structure:

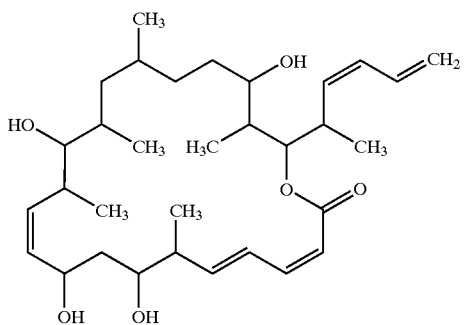

Specifically exemplified herein is the use of dictyostatin-1 and/or salts, analogs, and derivatives thereof, for immunomodulation, control of inflammation, inhibiting cellular proliferation, stabilization of microtubules, induction of polymerization of tubulin and/or inhibiting cellular proliferation of multi-drug resistant cells.

A further aspect of the subject invention is an efficient process of obtaining dictyostatins from the lithistid sponge of the family Corallistidae.

BRIEF DESCRIPTION OF THE DRAWINGS

The file of this patent contains at least one drawing executed in color. Copies of this patent with color drawings (s) will be provided by the Patent and Trademark Office upon request and payment of the necessary fee.

DETAILED DISCLOSURE OF THE INVENTION

Figure 1A:
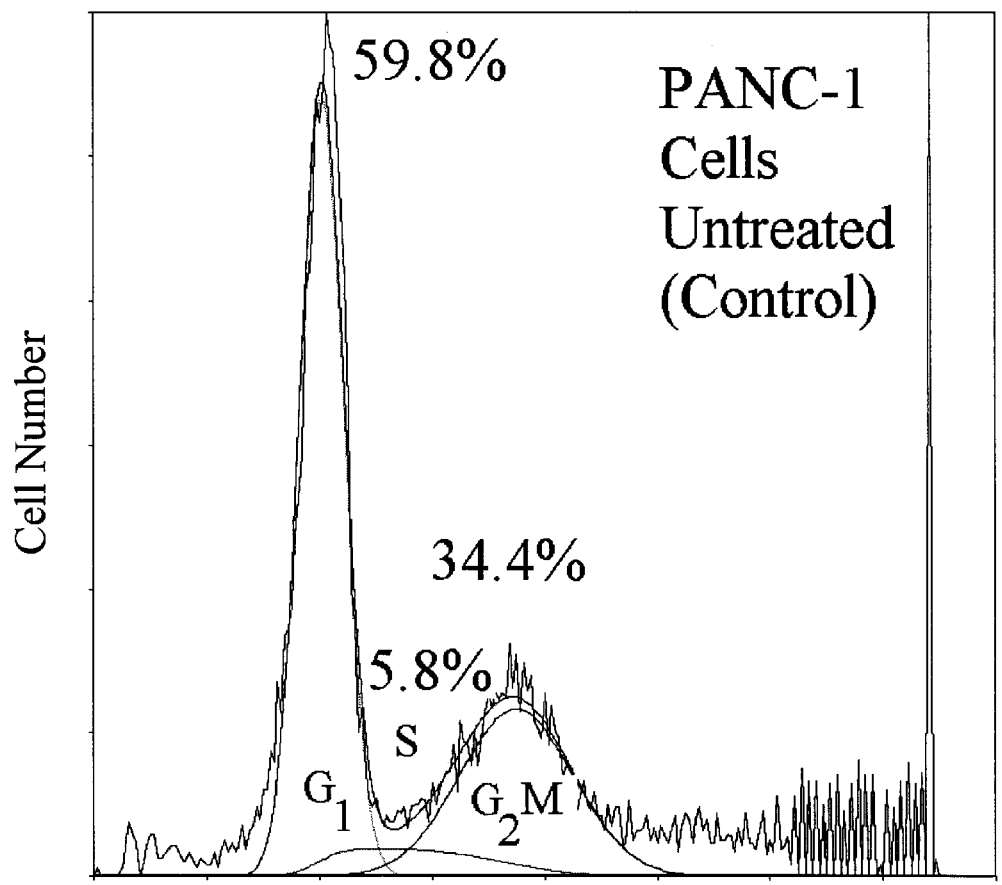
FIG. 1A shows that PANC-1 control cells (Untreated) exhibited a typical pattern of cell cycling, with a large percentage (59.8%) of the cell population comprising the $G_1$ population (first peak) with lesser percentages comprising both the S (5.8%) and $G_2$/M (34.4%) phases of the cell cycle.

The subject invention provides new uses for the dictyostatin class of compounds. These new uses include the control of cellular proliferation, cytotoxicity against human tumor cells resistant to chemotherapeutic agents, immunomodulation, and the control of inflammation. These uses arise from the identification of the role of dictyostatin compounds as tubulin polymerizers and microtubule stabilizers.

The dictyostatin class of compounds can be isolated from Dictyoceratid sponges of the genus Spongia. In accordance with the subject invention, it has now been determined that these compounds can also be isolated from a lithistid sponge of the family Corallistidae. The yield of compound from this organism is greatly increased over that reported from Spongia and represents an improved production of the subject compounds. (Yield from Corallistidae: $2.0 \times 10^{-3}$% of wet weight; yield from Spongia sp.: $3.2 \times 10^{-7}$% of wet weight.)

In a preferred embodiment, the dictyostatin compound of the subject invention has the following structure:

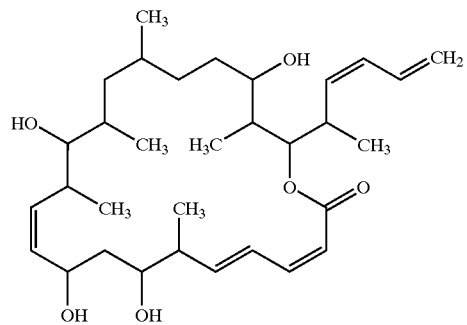

Specifically exemplified herein is the use of dictyostatin-1 and/or salts, analogs, and derivatives thereof, for immunomodulation, control of inflammation, stabilization of microtubules, induction of polymerization of tubulin, inhibiting cellular proliferation, and/or inhibiting cellular proliferation of multi-drug resistant tumor cells.

As used in this application, the terms "analogs" and "derivatives" refer to compounds which are substantially the same as another compound but which may have been modified by, for example, adding side groups, oxidation or reduction of the parent structure. Salts are also within the scope of the present invention. Analogs or derivatives of the exemplified compounds can be readily prepared using commonly known standard reactions. These standard reactions include, but are not limited to, hydrogenation, alkylation, acetylation, and acidification reactions.

In further preferred embodiments of the invention, salts within the scope of the invention are made by adding mineral acids, e.g., HCl, $H_2SO_4$, or strong organic acids, e.g., formic, oxalic, in appropriate amounts to form the acid addition salt of the parent compound or its derivative. Also, synthesis type reactions may be used pursuant to known procedures to add or modify various groups in the preferred compounds to produce other compounds within the scope of the invention.

In one embodiment, the subject invention pertains to the immunosuppressive use of the subject compounds. These compounds can be used to reduce, suppress, inhibit, or prevent unwanted immune responses. Thus, the compounds of the subject invention are useful for treatments of humans or animals requiring immunosuppression. Examples of conditions for which immunosuppression is desired include, but are not limited to, treatment or prevention of autoimmune diseases such as diabetes, lupus, and rheumatoid arthritis. Immunosuppression is also frequently needed in conjunction with organ transplants. Immunosuppressive agents can also be utilized when a human or animal has been, or may be, exposed to superantigens or other factors known to cause overstimulation of the immune system. The compounds of the subject invention are also useful as standards to assess the activity of other putative immunosuppressive agents.

The examples which follow are not meant to be fully inclusive of all methods which could be used to purify the subject compounds, but rather should be taken as examples of methods which can be used. A scientist skilled in the art of natural products purification could easily adapt the methods described and substitute a variety of solvents and stationary phases for those described in the preferred embodiment of the invention. In addition to chromatography, methods such as crystallization and partitioning can also be used to purify the desired compounds.

EXAMPLE 1

Collection of Sponge Source Material

A sample of Corallistidae (Phylum: Porifera, Class Demospongiae, Order Lithistida, Family Corallistidae) was collected at a depth of 442 m off the North Jamaican Coast (latitude 18 28.638'N, longitude78 10.996'W). The sponge morphology is that of a stalked cup with a smooth surface and a warty-lumpy underside, stony in consistency, and white in color. A reference sample preserved in ethanol has been deposited in the Harbor Branch Oceanographic Museum (catalog number 003:00959, DBMR number 23-VIII-93-5-008) and is available for taxonomic evaluation by those skilled in the art.

EXAMPLE 2

Isolation of Dictyostatin-1

Two-hundred (200) grams of the frozen Corallistidae sponge, 23-VIII-93-5-008 were extracted exhaustively by macerating with ethanol using a Waring Blender (5×200 mL). The combined filtered extracts were concentrated by distillation under reduced pressure to yield 5.66 crude orange residue. The residue was partitioned between n-butanol and water. After concentration, the n-butanol phase (0.69 g) was chromatographed under vacuum column chromatographic conditions on an Kieselgel 60 H (EM SCIENCE) stationary phase. A 150 mL Buchner funnel fitted with a medium porosity fritted glass disc was used as the column. The stationary phase was packed to a total height of 4 cm. The butanol partition was applied as a slurry to the column in a mixture of heptane-ethyl acetate containing a trace of methanol. Fractions were eluted using a 25% step gradient of ethyl acetate in heptane followed by a series of fractions containing increasing amounts of methanol in ethyl acetate [Fraction 1: heptane (100 ml); Fraction 2: heptane-ethyl acetate 75:25 v/v (100 ml); Fraction 3: heptane-ethyl acetate 50:50 v/v (100 ml); Fraction 4: heptane-ethyl acetate 25:75 v/v (100 ml); Fraction 5: ethyl acetate (100 ml); Fraction 6: ethyl acetate-methanol 95:5 v/v (100 ml); Fraction 7: ethyl acetate-methanol 90:10 v/v (100 ml); Fraction 8: ethyl acetate-methanol 25:75 v/v (100 ml); Fraction 9 methanol (100 ml). Fractions 4 and 5 contained dictyostatin-1 with the majority of the compound in Fraction 4.

Dictyostatin-1 was further purified by MPLC using a 1×25 cm Altex column custom packed at HBOI using a bulk Vydac Protein and Peptide $C_{18}$ stationary phase, 20–30 mm particle, Cat No 218TPB. A Gilson fraction collector was used to collect fractions dropwise with a total of 350 drops per fraction (volume=10 ml), flow rate 5 ml/minute. The column was eluted with a step gradient of acetonitrile in water as follows: Fractions 2–24 eluted with water/acetonitrile 8:2 v/v; Fractions 25–50 eluted with water/acetonitrile 6:4 v/v; Fractions 51–75 eluted with water/acetonitrile 4:6 v/v; Fractions 76–80 eluted with 100% acetonitrile.

Twenty microliters of each fraction was analyzed using the following gradient HPLC analysis: Hitachi LaChrom L-7100 pump with an L-7455 PDA detector and D-7000 interface. Column: Vydac Protein and Peptide $C_{18}$ Column (4.6 mm×250 mm, pore size 300 A, 10 mm particle size), eluted with a linear gradient: flow rate=1 ml/minute; Solvent A=Water-Acetonitrile 95:5 v/v; Solvent B=Acetonitrile; time 0: A:B 80:20 v/v B; time=15 minutes 100% B; time=20 minutes 100% B; time=22 minutes 50% A, 50% B. Under these conditions, dictyostatin-1 elutes after 6.5 column volumes and has a distinctive UV absorbance profile with double absorbance maxima observed at $I_{max}$ 227.5 and 266.6. Dictyostatin-1 was detected in MPLC fractions 57 and 58 under these HPLC conditions.

The structure of dictyostatin-1 was defined by NMR spectroscopy and found to be nearly identical to the data reported by Pettit et. al. (G. R. Pettit, Z. A. Cichacz, F. Gao, M. R. Boyd and J. M. Schmidt, Isolation and Structure of the Cancer Cell Growth Inhibitor dictyostatin-1, *J. Chem. Soc. Chem. Comm.* 1994, 1111–1112 ) for dictyostatin-1. Table 1 lists the published data and the data observed for this isolation of dictyostatin-1.

TABLE 1

Comparison of $^{13}C$ and $^1H$ NMR data observed for the current isolation of Dictyostatin-1, to that reported by Pettit et al. (J. Chem. Soc. Chem. Comm. [1994] pgs 1111–1112). New data was obtained in $CD_3OD$.

| Atom # | $^{13}C$ NMR (125 MHZ) δ | | $^1H$ NMR (500 MHZ) δ | |
|---|---|---|---|---|
| | Literature | HBOI isolation | Literature | HBOI isolation |
| 1 | 168.1 | 168.06 | | |
| 2 | 118.03 | 118.53 | 5.52 | 5.51 |
| 3 | 144.89 | 144.84 | 6.62 | 6.62 |
| 4 | 128.58 | 128.55 | 7.17 | 7.18 |
| 5 | 146.42 | 146.38 | 6.14 | 6.16 |
| 6 | 44.05 | 44.03 | 2.57 | 2.57 |
| 7 | 70.37 | 70.39 | 4.02 | 4.03 |
| 8 | 40.59 | 40.65 | 1.48, 1.38 | 1.48, 1.38 |
| 9 | 65.5 | 65.49 | 4.62 | 4.63 |
| 10 | 134.89 | 134.79 | 5.37 | 5.38 |
| 11 | 131.32 | 131.26 | 5.52 | 5.52 |
| 12 | 35.74 | 35.74 | 2.72 | 2.73 |
| 13 | 80.37 | 80.38 | 3.06 | 3.09 |
| 14 | 35.32 | 35.276 | 1.58 | 1.58 |
| 15 | 42.26 | 42.23 | 1.22, 0.88 | 1.22, 0.87 |
| 16 | 31.22 | 31.17 | 1.5 | 1.51 |
| 17 | 32.74 | 32.7 | 1.56, 0.68 | 1.53, 0.68 |
| 18 | 32.5 | 32.44 | 1.82, 1.08 | 1.81, 1.06 |
| 19 | 73.72 | 73.68 | 3.33 | 3.36 |
| 20 | 40.82 | 40.79 | 1.86 | 1.86 |
| 21 | 78.63 | 78.59 | 5.1 | 5.09 |
| 22 | 35.82 | 35.79 | 3.13 | 3.14 |
| 23 | 134.53 | 134.49 | 5.3 | 5.29 |
| 24 | 131.22 | 131.26 | 6.02 | 6.02 |
| 25 | 133.43 | 133.37 | 6.67 | 6.68 |
| 26 | 118.58 | 118.51 | 5.21, 5.11 | 5.2, 5.11 |
| 27 | 13.75 | 13.81 | 1.11 | 1.115 |
| 28 | 19.35 | 19.3 | 1.09 | 1.09 |
| 29 | 15.97 | 15.91 | 0.92 | 0.921 |
| 30 | 21.81 | 21.74 | 0.89 | 0.883 |
| 31 | 10.39 | 10.36 | 1.03 | 1.032 |
| 32 | 18.06 | 18.03 | 0.98 | 0.989 |

EXAMPLE 3

Effect of dictyostatin-1 on Cell Cycle Progression of PANC-1 Human Pancreatic Adenoma Cells in Comparison to Taxol Cell cycle studies were initiated in order to pinpoint a specific phase within the cell cycle in which dictyostatin-1 was exerting its antiproliferative effect. PANC-1 human pancreatic adenoma cells were used as cell cycle targets to compare the effects on perturbation of the cell cycle of dictyostatin-1 to the known mitotic spindle inhibitor discodermolide. Cell cycle analyses were performed as follows: PANC-1 cells were incubated at 37° C. in 5% $CO_2$ in air in the presence or absence of varying concentrations of dictyostatin-1 or Taxol for 24 hours.

Cells were harvested, fixed in ethanol and stained with 0.02 mg/ml of propidium iodide (P.I.) together with 0.1 mg/ml of RNAse A. This procedure permeabilizes cells and allows entry of P.I. to stain DNA (propidium iodide also stains double stranded RNA, so RNAse is included in the preparation to exclude this possibility). Stained preparations were analyzed on a Coulter EPICS ELITE with 488 nm excitation. Fluorescence measurements and resulting DNA histograms were collected from at least 3,000 P.I. stained cells at an emission wavelength of 690 nM. Raw histogram data was further analyzed using a cell cycle analysis program (Multicycle, Phoenix Flow Systems).

Figure 1B:
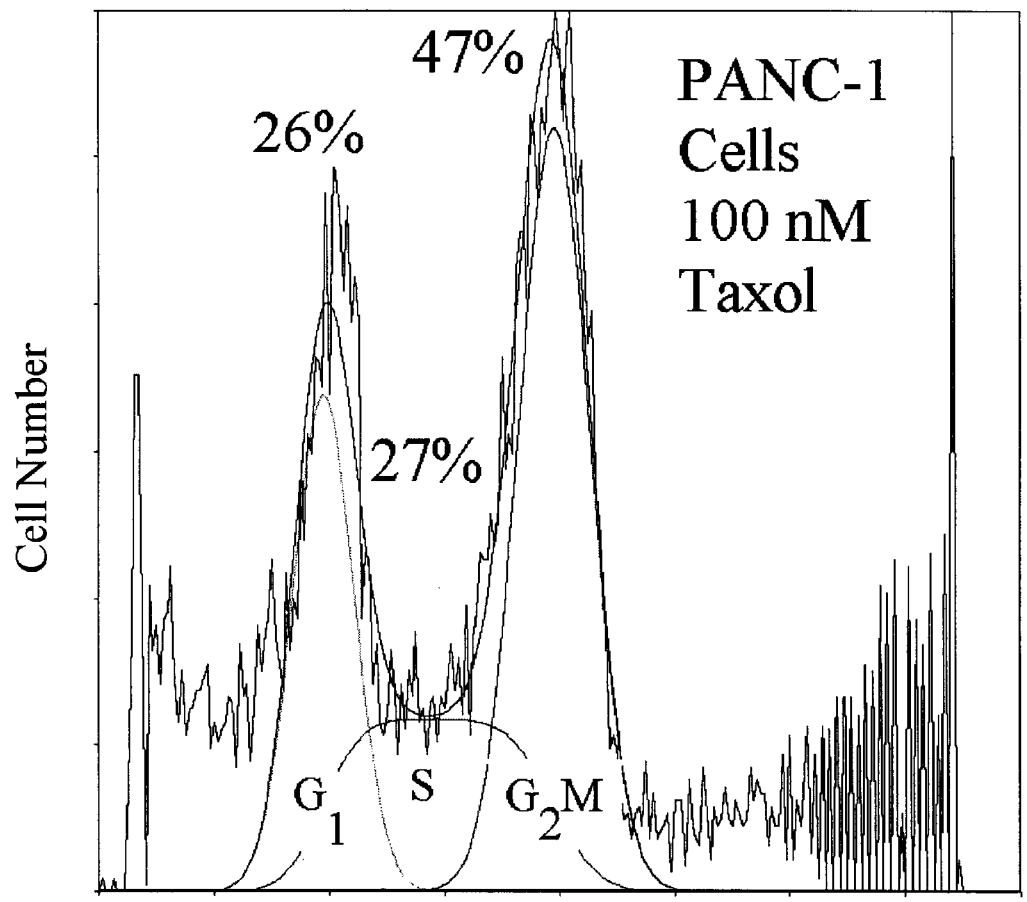
FIG. 1B shows that PANC-1 cells treated with 100 nM Taxol exhibited decreased percentages of cells comprising the $G_1$ population and corresponding increased percentages in both S and $G_2$/M phases of the cell cycle indicating Taxol's ability to induce $G_2$/M block. Cells undergoing apoptosis are also evident as a peak immediately to the left of the $G_1$ peak.
Figure 1C:
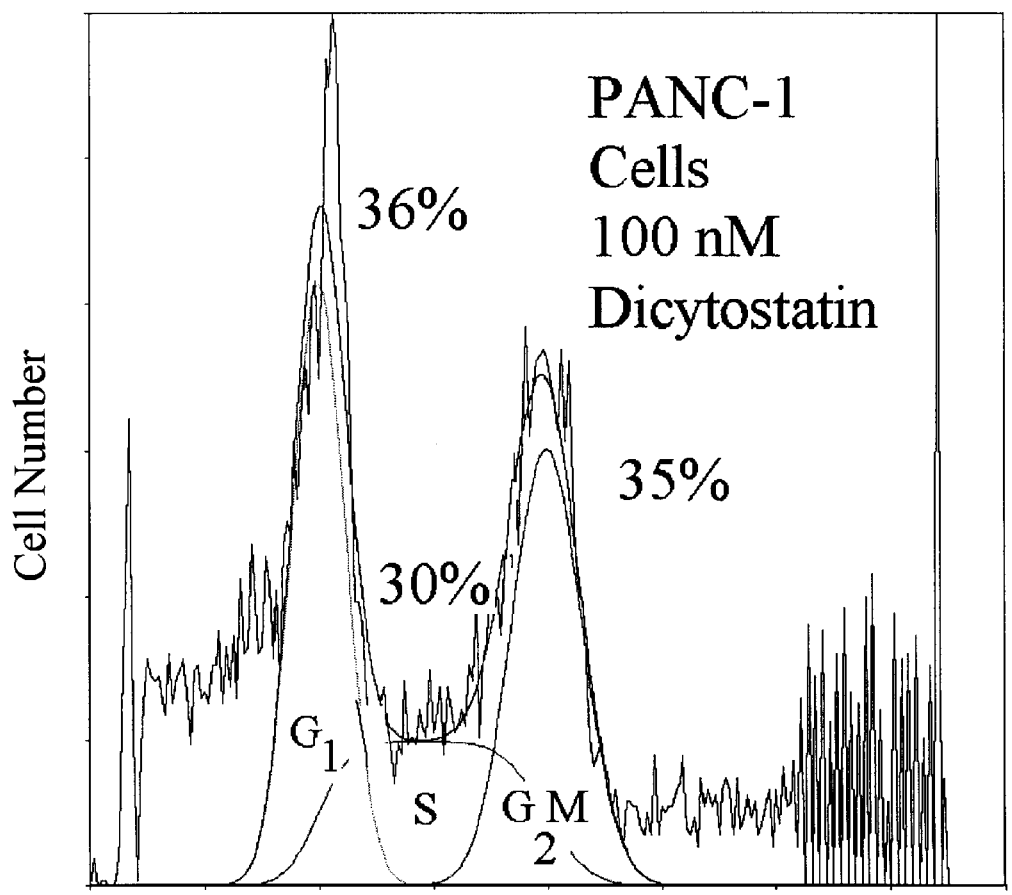
FIG. 1C shows that PANC-1 cells treated with 100 nM Dictyostatin-1 exhibited decreased percentages of cells comprising the $G_1$ population and corresponding increased percentages in both S and $G_2$/M phases of the cell cycle indicating dictyostatin's ability to induce $G_2$/M block.

The results of these experiments are shown in FIGS. 1A, 1B and 1C. FIG. 1A shows that PANC-1 control cells (Untreated) exhibited a typical pattern of cell cycling, with a large percentage (59.8%) of the cell population comprising the $G_1$. population (first peak) with lesser percentages comprising both the S (5.8%) and $G_2/M$ (34.4%) phases of the cell cycle. FIG. 1B shows that PANC-1 cells treated with 100 nM Taxol exhibited decreased percentages of cells comprising the $G_1$ population (26%) and corresponding increased percentages in both S (27%) and $G_2/M$ (47%) phases of the cell cycle indicating Taxol's ability to induce $G_2/M$ block. Cells undergoing apoptosis are also evident as a peak inimediately to the left of the $G_1$ peak. FIG. 1C shows that PANC-1 cells treated with 100 nM dictyostatin-1 exhibited decreased percentages of cells comprising the $G_1$ population (36%) and corresponding increased percentages in both S (30%) and $G_2/M$ (35%) phases of the cell cycle indicating dictyostatin's ability to induce $G_2/M$ block.

EXAMPLE 4

Immunofluorescent Detection of Effects on the Microtubule Matrix in Tumor Cells Dictyostatin-1 was evaluated as to its effects on the microtubule network of cells using anti-alpha-tubulin monoclonal antibodies. Cells treated with the anti-cancer drug Taxol, routinely exhibit abnormal formation of multiple centriolar-radiating microtubules with extensive clusters of associated microtubular "bundles", unlike the fine "mesh" of individual microtubules which make up the cytoskeletal network.

PANC-1 human pancreatic adenocarcinoma cells were maintained in tissue culture media (TCM=Roswell Park Memorial Institute (RPMI) medium 1640 supplemented with 100 U/ml penicillin, 100 mg/ml streptomycin, 60 mg/ml 1-glutamine, 18 mM HEPES, 0.05 mg/ml gentamicin and 10% fetal bovine serum) and cultured in plastic culture flasks at 37° C. in humidified air containing 5% $CO_2$. Stock cultures of PANC-1 cells were subcultured 1:10 every 3 to 4 days. On day 1, 1.25×10$^5$ PANC-1 cells were sub-cultured in TCM overnight at 37° C. in 5% $CO_2$ on 22 mm$^2$ coverslips in 6-well microtiter plates. On day 2, TCM was removed and replaced with various concentrations of dictyostatin-1, or Taxol, in TCM or TCM without drug (control) and incubated overnight at 37° C. in 5% $CO_2$. On day 3, TCM was removed and cells attached to coverslips were fixed with a 3.7% formaldehyde solution in Dulbecco's PBS for 10 minutes at room temperature. Cells were permeabilized with a 2% Triton X-100 solution, 2 ml per well, for 5 minutes at room temperature and washed twice in Dulbecco's PBS prior to staining.

To each well containing cells attached to coverslips a 2 ml volume of mouse monoclonal anti-alpha-tubulin (Cat #T-5168, Sigma Chemical Co.) diluted 1:1000 in Dulbeccos phosphate buffered saline (D-PBS) was added and the cells incubated at room temperature for 45 minutes. A 2 ml volume of goat-anti-mouse-IgG-FITC conjugate (Cat #T-5262, Sigma Chemical Co.) diluted 1:1000 in D-PBS was added and the cells incubated at room temperature for 45 minutes. Coverslips were rinsed three times with sterile distilled water, air-dried and mounted on slides and observed under the microscope using epifluorescence illumination for the presence of abnormal aster and microtubule formation.

Figure 2A:
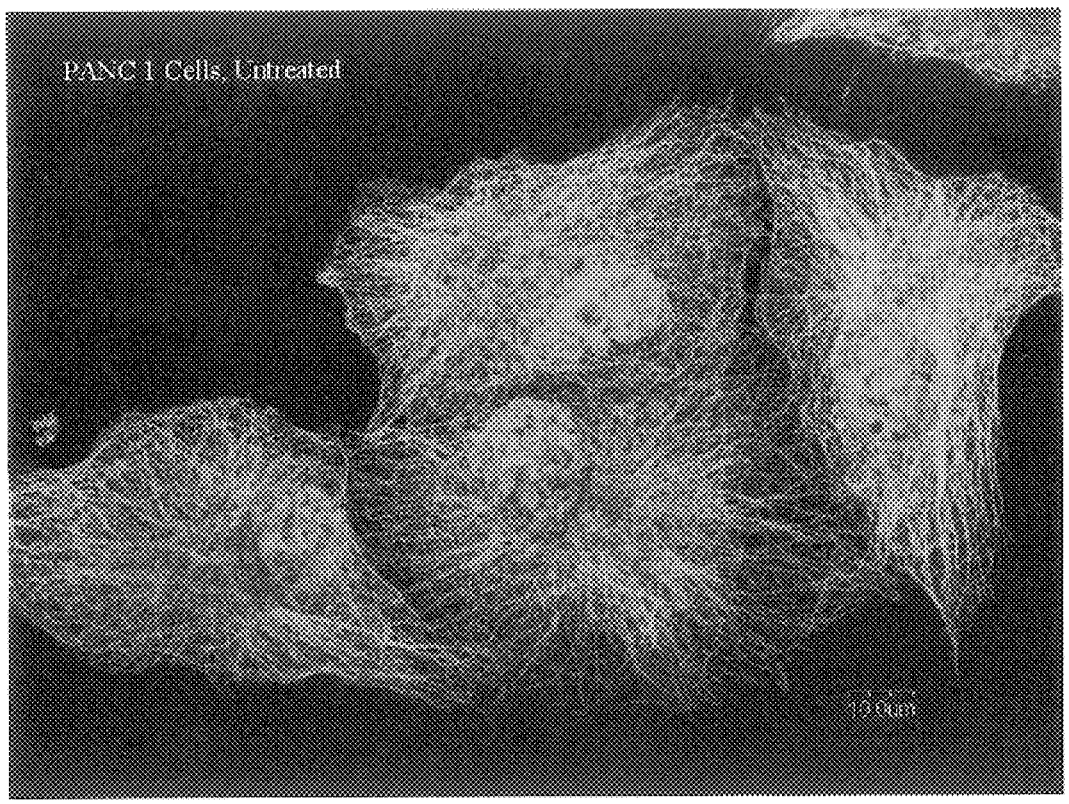
FIG. 2A shows a PANC-1 cell preparation with characteristic staining of individual microtubules with fluorescent anti-alpha-tubulin indicated by a fine network "mesh" of microtubular material. Nuclei are uniform and rounded as indicated by red staining with propidium iodide.
Figure 2B:
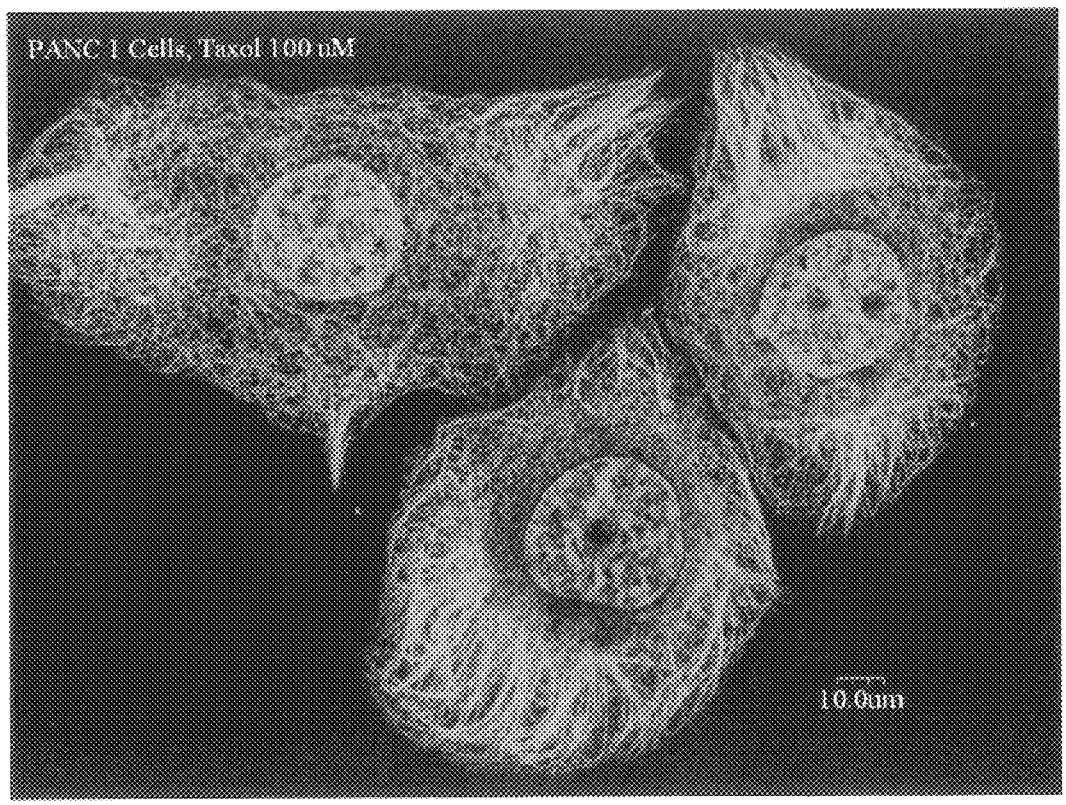
FIG. 2B shows corresponding PANC-1 cells treated with 100 nM taxol and exhibiting the characteristic formation of microtubular "bundles" but also a substantial amount of "non-bundled" microtubular material still remained in the cytoplasm.
Figure 2C:
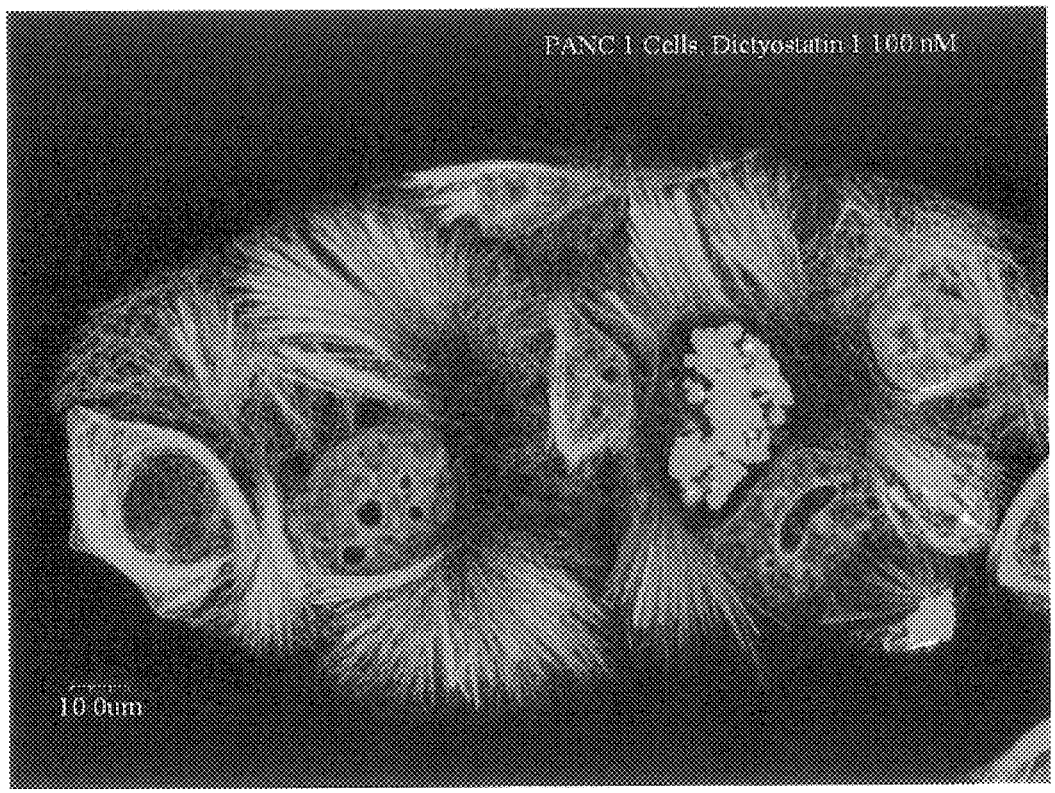
FIG. 2C shows corresponding PANC-1 cells treated with 100 nM Dictyostatin-1 and exhibiting extensive microtubule bundling resulting in almost complete depletion of non-bundled microtubular material in the cytoplasm.

The results of these experiments are shown in FIGS. 2A, 2B, and 2C. FIG. 2A shows a PANC-1 cell preparation with characteristic staining of individual microtubules with fluorescent anti-alpha-tubulin indicated by a fine network "mesh" of microtubular material. Nuclei are uniform and rounded as indicated by red staining with propidium iodide. FIG. 2B shows corresponding PANC-1 cells treated with 100 nM Taxol and exhibiting the characteristic formation of microtubular "bundles" but also a substantial amount of "non-bundled" microtubular material still remained in the cytoplasm. FIG. 2C shows corresponding PANC-1 cells treated with 100 nM dictyostatin-1 and exhibiting extensive microtubule bundling resulting in almost complete depletion of non-bundled microtubular material in the cytoplasm.

EXAMPLE 5

Cytotoxic Effects of dictyostatin-1 on Taxol Resistant Cell Lines

The cytotoxicity of dictyostatin-1 for various Taxol resistant and sensitive cell lines was compared to that of Taxol. The cell lines used were A549 human adenocarcinoma, MCF-7 human breast carcinoma, MCF-7ADR multi-drug resistant (Taxol resistant) human breast carcinoma, MES-SA human uterine carcinoma and MES-SA/DX5 Taxol resistant uterine carcinoma. All cell lines were maintained in Roswell Park Memorial Institute (RPMI) medium 1640 supplemented with 100 U/ml penicillin, 100 mg/ml streptomycin, 60 mg/ml 1-glutamine, 18 mM HEPES, 0.05 mg/ml gentamicin (Life Technologies, Gaithersburg, Md.) and 10% fetal bovine serum and cultured in plastic tissue culture flasks at 37° C. in humidified air containing 5% $CO_2$. Stock cultures of cells were subcultured 1:10 every 3 to 4 days. To assess the antiproliferative effects of agents against the cells, 200 μl cultures (96-well tissue culture plates, Nunc, Denmark) were established at $1 \times 10^5$ cells/mL in TCM or TCM containing the test agent at 0.03–5.0 μg/ml. After 72-h exposures, the effects of dictyostatin-1 and Taxol on cell proliferation were quantitated and $IC_{50}$ values determined as follows: 75 μl of warm growth media containing 5 mg/ml 3-[4,5-dimethylthiazol-2-yl]-2,5-diphenyltetrazolium bromide (MTT) (M. C. Alley et al. (1988) Cancer Res. 48:589) was added to each well, cultures returned to the incubator, and left undisturbed for 3 hours. To spectrophotometrically quantitate formation of reduced formazan, plates are centrifuged (500×g, 10 minutes), culture fluids removed by aspiration, and 200 μl of acidified isopropanol (2 ml concentrated HC1/liter isopropanol) added per well. The absorbance of the resulting solutions is measured in a plate reader (Tecan Spectra SLT; TECAN U.S., Research Triangle Park, N.C.) at 570 nm and a 650 nm reference filter. The absorbance of tests wells is divided by the absorbance of drug-free wells, and the concentration of agent that results in 50% of the absorbance of untreated cultures ($IC_{50}$) is determined by linear regression of logit-transformed data (D. J. Finney, Statistical Method in Biological Assay, Third Ed., pp.316–348, Charles Griffin Co., London, 1978). A linear relationship between tumor cell number and formazan production has been routinely observed over the range of cell densities observed in these experiments. The two standard drug controls (indicated above) are included in each assay as a check to monitor the drug sensitivity of each of the cell lines and $IC_{50}$ values are determined for each drug-cell combination.

The results in Table 2 show that the cytotoxic activity of dictyostatin-1 was very similar to that of Taxol (in the low nanomolar range) in the cell lines which were sensitive to Taxol (MCF-7 and MES-SA). However, in the Taxol resistant counterparts, cells exhibited very low resistance to dictyostatin-1 (13-fold and 3-fold for MCF-7ADR and MES-SA/DX5, respectively) whereas their resistance was much greater to Taxol (1332-fold and 501-fold for MCF-7ADR and MES-SA/DX5, respectively). These results indicate that dictyostatin-1, a tubulin interactive compound, which induces $G_2/M$ block and causes the hyperstabilization of microtubules in cells, possess properties which allow it to kill tumor cells which have developed resistance to anticancer agents.

TABLE 2

Cytotoxicity of Dictyostatin-1 and Taxol for Various Taxol-resistant and Sensitive Cell Lines

| | nM $IC_{50}$ (Std dev) | | | | |
|---|---|---|---|---|---|
| | A549 | MCF-7 | MCF-7/ADR | MES-SA | MES-SA/DX5 |
| Taxol | 5.13 (2.9) | 2.5 (0.7) | 3331 (652) | 3.3 (0.6) | 1654 (230) |
| Resistance: | | | 1332× | | 501× |
| Dictyostatin-1 | 0.95 (0.25) | 1.5 (0.9) | 20 (4.2) | 4.1 (1.4) | 11 (2.4) |
| Resistance: | | | 13× | | 3× |

EXAMPLE 6

Polymerization of Tubulin

Polymerization of purified bovine brain tubulin (Cytoskeleton Inc., Denver, Co.) was followed by changes in the optical density of tubulin solutions at 350 nm in a Hitachi U-3010 spectrophotometer equipped with a SPR-10 electronic thermostatted cell holder. Stock solutions of tubulin were diluted on ice in G-PEM buffer (1 mM GTP, 80 mM PIPES (piperazine-N,N'-bis(2-ethanesulfonic acid] sesquisodium salt), 1 mM EGTA (ethylene glycol-bis(b-amine ethyl ether) N,N,N,N'-tetra acetic acid), 0.5 mM magnesium chloride; pH 6.8) to a final concentration of 1 mg/ml. The instrument was zeroed on this solution at 4° C. Dictyostatin-1, was then added to the tubulin to a final concentration of 10 μM and quickly mixed. The polymerization was monitored by observing light scattering changes in optical density at 350 nm using the spectrophotometer. The temperature was varied for a time period of 61 minutes beginning at 4° C. for 1 minute, then linearly ramping to 35° C. over 30 minutes, with a hold of one minute at 35° C., then linearly decreasing to 4° C. over 15 minutes, with this temperature being maintained for an additional 15 minutes. Absorbance was measured and recorded over the entire time period.

Figure 3:
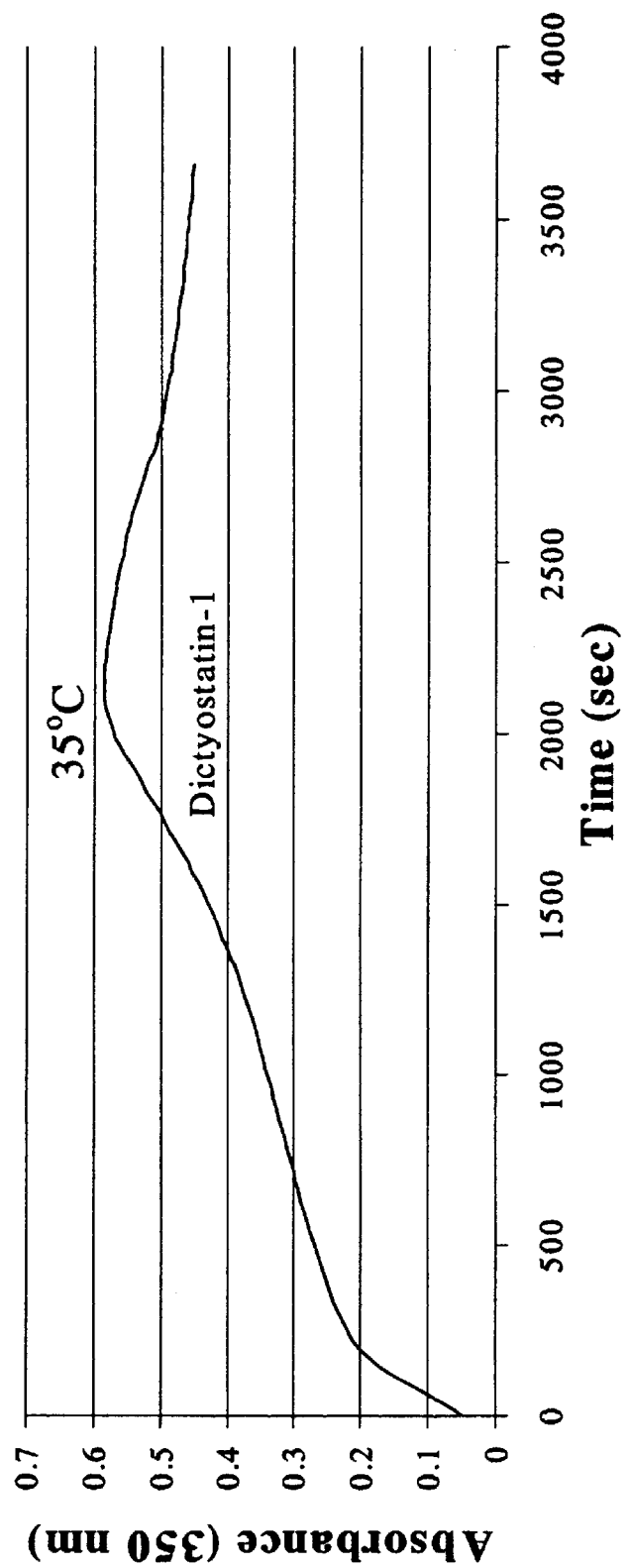
FIG. 3 shows the polymerization of tubulin by Dictyostatin-1.

Dictyostatin-1 induced tubulin polymerization with a maximum polymerization level reached at 35° C. Once polymerized, the tubulin did not substantially depolymerize upon reduction of the temperature. The results of these experiments are shown in FIG. 3.

EXAMPLE 7

Formulation and Administration

The compounds of the invention are useful for various non-therapeutic and therapeutic purposes. It is apparent from the testing that the compounds of the invention are effective for inhibiting cell growth. Because of the antiproliferative properties of the compounds, they are useful to prevent unwanted cell growth in a wide variety of settings including in vitro uses. They are also useful as standards and for teaching demonstrations. They can also be used as ultraviolet screeners in the plastics industry since they effectively absorb UV rays. As disclosed herein, they are also useful prophylactically and therapeutically for treating cancer cells in animals and humans.

Therapeutic application of the new compounds and compositions containing them can be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the cancer cells, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, Remington's Pharmaceutical Science by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the new compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

To provide for the administration of such dosages for the desired therapeutic treatment, new pharmaceutical compositions of the invention will advantageously comprise between about 0.1% and 45%, and especially, 1 and 15%, by weight of the total of one or more of the new compounds based on the weight of the total composition including carrier or diluent. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

These data indicate that the dictyostatin class of metabolites are potent inducers of tubulin polymerization and stabilizers of the microtubule network. This activity is useful in the treatment of diseases caused by proliferation of cells including autoimmune and inflammatory processes. Moreover, these data indicate that the dictyostatin class of metabolites are useful in the treatment of multi-drug resistant tumors where resistance is caused by either the pGp or MRP resistance mechanisms.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for the inhibition of cellular proliferation in autoimmune disorders and inflammatory diseases wherein said method comprises administering an effective amount of dictyostatin-1, or salt thereof, to a human or animal in need of such treatment.

2. The method, according to claim 1, wherein the following compound is administered:

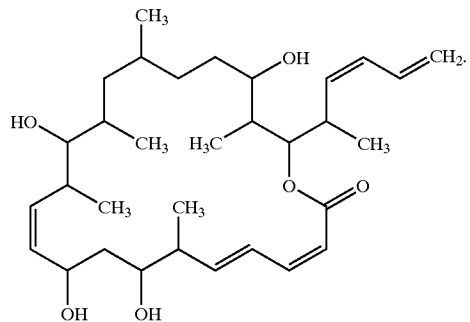

3. The method, according to claim 1, wherein said method is used in the prevention or treatment of a condition selected from the group consisting of diabetes, lupus and rheumatoid arthritis.

4. The method, according to claim 1, wherein said method is used for immunosuppression in conjunction with organ transplants.

5. A method for the induction of polymerization of tubulin and the stabilization of microtubules in non-cancer cells by administering to said cells an effective amount of dictyostatin-1 or salt thereof.

6. The method, according to claim 5, wherein the following compound is administered:

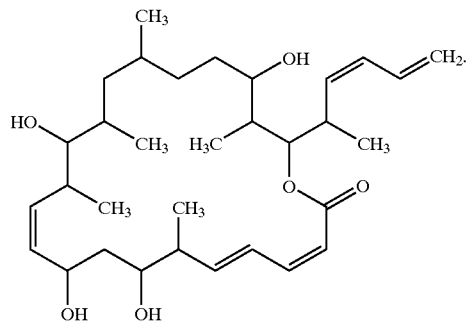

* * * * *